United States Patent [19]

Berger

[11] Patent Number: 5,354,321
[45] Date of Patent: Oct. 11, 1994

[54] PATCH ARRANGEMENT FOR GALVANIC TREATMENT

[76] Inventor: Mario Berger, Gartenstrasse 15, 5788 Winterberg, Fed. Rep. of Germany

[21] Appl. No.: 859,691
[22] PCT Filed: Oct. 1, 1991
[86] PCT No.: PCT/DE91/00772
   § 371 Date: Jun. 10, 1992
   § 102(e) Date: Jun. 10, 1992
[87] PCT Pub. No.: WO92/06736
   PCT Pub. Date: Apr. 30, 1992

[30] Foreign Application Priority Data

Oct. 10, 1990 [DE] Fed. Rep. of Germany ....... 4032109
May 6, 1991 [DE] Fed. Rep. of Germany ....... 4114677

[51] Int. Cl.$^5$ ............................................. A61N 1/04
[52] U.S. Cl. .................... 607/75; 607/115; 607/152
[58] Field of Search ............. 607/75, 115, 149, 152

[56] References Cited

U.S. PATENT DOCUMENTS 4,776,350 10/1988 Grossman et al. ................. 607/152
4,895,169 1/1990 Heath ................................ 607/152
5,024,227 6/1991 Schmid ............................. 607/152

Primary Examiner—Lee S. Cohen
Attorney, Agent, or Firm—Feiereisen & Kueffner

[57] ABSTRACT

The invention refers to a patch arrangement for electric elimination of muscle spasms. The invention is based upon the object to employ electrotherapy through stable galvanization without external voltage source to attain high efficiency and to make it overall more practical. In accordance with the invention, the object is attained by arranging a plane electrode of different metals at both sides of the affected area. A further metal electrode is applied onto both of these skin contact electrodes at the other side or body-distant side thereof wherein the metals of these electrodes may correspond to those of both skin electrodes, however, with opposing polarity according to the electrochemical series. Both obtained compact bimetallic electrodes are insulated at their border against electrolytic shorting and attached to the body by means of the electrocardiographic electrode patch which is available in the medical trade. Moreover, by suitably selecting the metals, two additional galvanic elements are obtained upon the skin in series with the galvanic element composed of two different metals and already known in the literature.

8 Claims, 3 Drawing Sheets

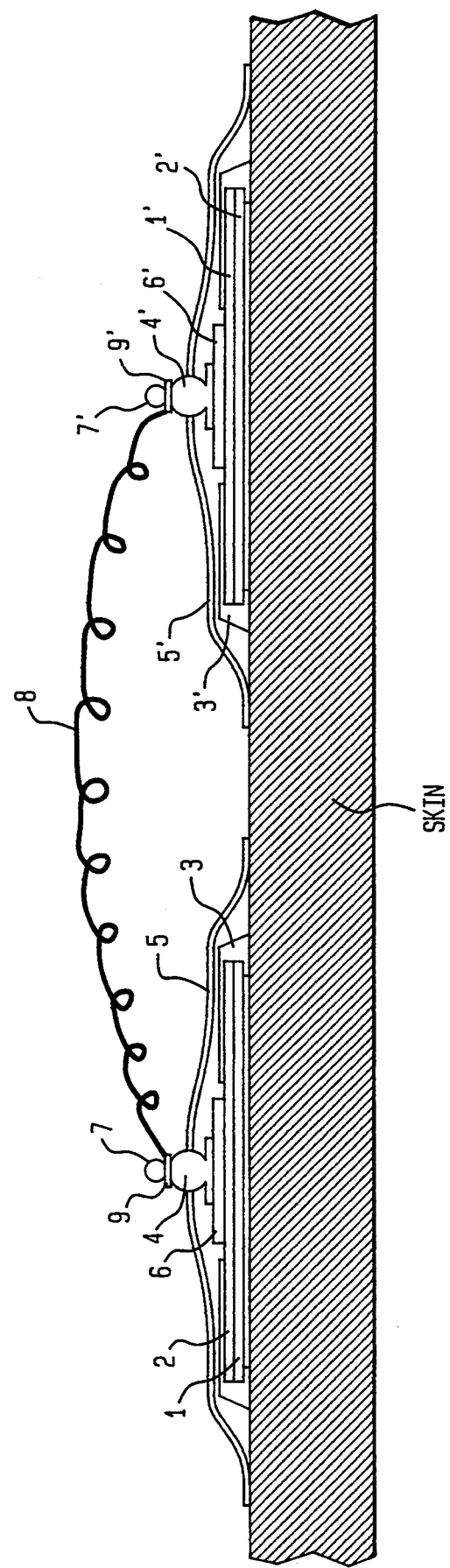

PATCH ARRANGEMENT FOR GALVANIC TREATMENT

BACKGROUND OF THE INVENTION

The invention refers to a patch arrangement of electrically connected electrodes of different metals for application upon the human body for electric influence of electrically acting structures of the organism.

When experiencing muscle spasms and irritations of the nerve root especially in the area of the spine, electrotherapy is increasingly the preferred treatment. The aversion of employing a respective drug therapy increases.

Application of a direct current through the tissue being treated (stable galvanization) is of particular significance. In practice, large stationary devices are used which are also dimensioned for other types of current (so-called stimulating current devices). Smaller portable and battery-operated devices (so called TENS-devices) are commercially available for ambulant or medium-term continuous application. While a longer-term application with stationary devices is not feasible, the still required size of portable devices renders their use still inconvenient.

Treatment of muscle spasms of all types with a comparably small permanent current in the μA-range has proven to be very effective. Various arrangements were thus described which utilize the potential difference between two differently noble metals which are in contact with the skin perspiration electrolytes for producing a current flow through the body tissue being treated. The arrangement according to GB-PS 3276 (1904) requires, however, very large skin electrodes for accomplishing a sufficient current flow. According to CH-PS 171866, the galvanic voltage is generated through different metal electrodes as well as skin perspiration electrolytes and/or different fabric layers soaked with electrolyte. In this context the use of adhesive coatings were also proposed, resulting in solutions which essentially constitute short-term utilizable, disposable articles with expensive metal electrodes.

GB-PS No. 288 of 1904 describes an alternate arrangement of superimposed disks of noble metal and base metal, with reference to galvanic intermediate layers between zinc and copper; however, there is no explanation with regard to the configuration of a closed circuit. Poor efficiency or impractical application are reasons that hitherto proposed technical solutions did not succeed.

SUMMARY OF THE INVENTION

The invention aims at an increase of the current density in connection with skin contact electrodes which are kept as small as possible, at a simple handling as well as at an economic manufacture and thus application, by using an already commercially available product which serves as inexpensive disposable article for attachment of the arrangement of electrodes upon the body surface and additionally for creating further galvanic elements to increase the voltage. The subject matter according to the invention which includes only the metal electrodes as the actual expensive part of the galvanic system and a border insulation should be reusable and should have a relatively long life.

This object is attained in accordance with the invention by initially arranging in a known manner a preferably round plane electrode of differently noble metals at each side of the ailing body areas.

BRIEF DESCRIPTION OF THE DRAWING

The above and other objects, features and advantages of the present invention will now be described in more detail with reference to the accompanying drawing in which:

FIG. 2 is a schematic side view of the patch arrangement of FIG. 1;

DETAILED DESCRIPTION OF PREFERRED EMBODIMENTS

Figure 1:
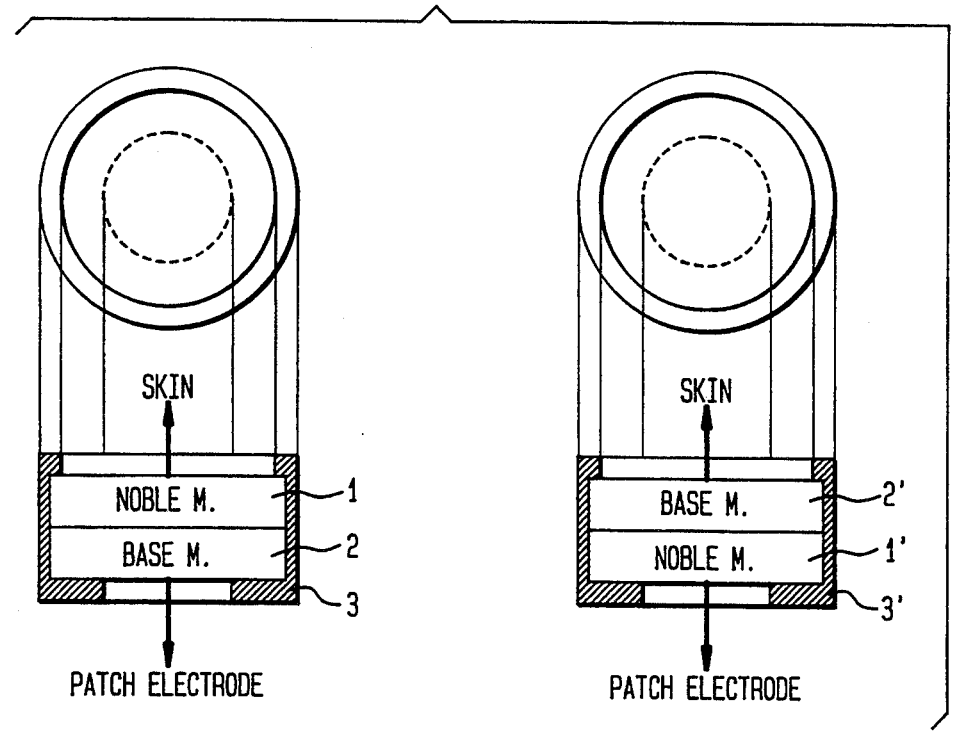
FIG. 1 is a schematic illustration of a patch arrangement according to the invention for application onto the skin for galvanic treatment.

Referring now to the drawing and in particular to FIG. 1, there is shown a schematic illustration of a patch arrangement according to the invention for application onto the skin for galvanic treatment, including a preferably round plane electrode of differently noble metals at each side of the ailing body areas.

A further metal electrode (2, 1') is applied onto both of these skin contact electrodes (1, 2') at the other side or body-distant side thereof wherein the metals of these electrodes may correspond to those of both skin electrodes (1, 2'), however, with opposing polarity according to the electrochemical series. Both thus-created compact bimetallic electrodes (1, 2 and 2', 1') must be insulated at their border (3, 3') against an electrolytic shorting (FIG. 1).

Thus, two bimetallic disks with border insulation are obtained which can easily be made and include the expensive part (metal) of an electrogalvanic system in most compact form which are reusable and have a long life and which are designed in such a manner that they can be supplemented to a closed biogalvanic system via a clip contact cable (8) with the use of conventional electrocardiographic electrode patches (5, 5').

This electrode patch (4, 5, 6, 7, and 4', 5', 6', 7', respectively) which is not part of the subject matter according to the invention thus contains all elements of the biogalvanic system that are suitable for one time use or are of limited effectiveness (patch 5, 5'; electrode gel 6, 6'). A very effective and also water-tight attachment is possible. Moreover, an additional galvanic element is respectively obtained upon the skin between a body-distant metal electrode (2, 1') and the silver electrode of a patch (4, 4') with the pertaining electrode gel (6, 6'), such as a silver chloride gel pad, in series to the galvanic element of two different metals (1, 2') as already known in the literature. By suitably selecting the metals, three galvanic elements are thus formed, with the series connection resulting in a significant voltage increase compared to previous arrangements. For closing the electric circuit between both push-button contacts (7, 7') of the electrode patches, an elastic electrically conductive cable (8) is preferably used which includes spring contact eyelets (9, 9') at its ends. By incorporating a variable resistor in this cable, the user is able to control the current.

FIG. 2 illustrates the structure of the above-described circuit as follows: skin—(1)—(2)—(6)—(4)—(7)—(9-)—(8)—(9')—(7')—(4')—(6')—(1')—(2')—skin.

Figure 3:
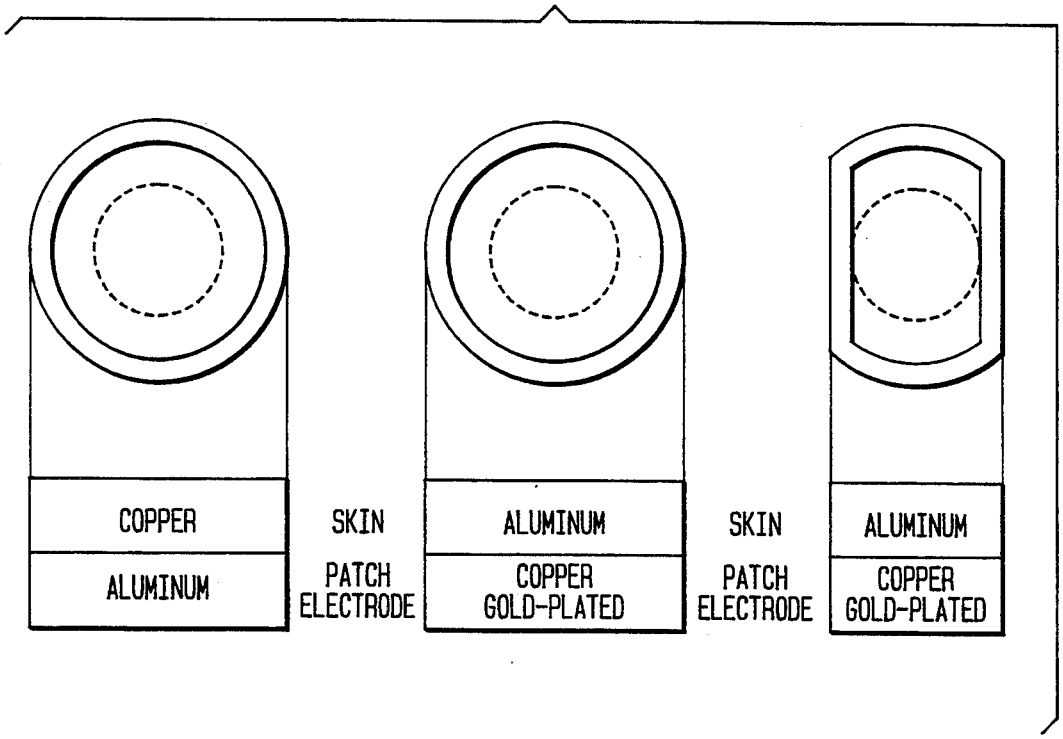
FIG. 3 is an illustration of an example of a patch arrangement according to the invention.

FIG. 3 refers to an exemplified embodiment. Based on the objective to eliminate muscular spasms especially in the straight back musculature and to eliminate the back pain and neck spasms frequently connected therewith in many people, the above-described arrangement of electrocardiographic electrode patch and double electrode is preferably applied at both sides of the aching area in longitudinal direction over the spine to remain there for a longer period (several days are possible).

Very effective currents can be generated when using suitable metals from the entire spectrum of the electrochemical series. The following sequence of metals would be recommended in connection with the described galvanic triple system (FIGS. 2 and 3):

Aluminum (1)—copper, gold plated (2)—silver chloride gel pad (6)—silver (4)—silver (4')—silver chloride gel pad (6')—aluminum (1')—copper, gold plated (2')—skin.

For commercial use, a set with three double electrodes would be conceivable. Two round ones for application onto the dorsal spine and lumbar spine and a narrower one for direct attachment onto the hairline on the back of the neck when symptoms are encountered in the shoulder and neck area. In the latter case of application, one of the round double electrodes is respectively used in addition (FIG. 3).

The elastic and electrically conductive cable may be made of a strip of rubber with copper wire strands applied thereon and with the clip contact eyelets (9, 9') mounted at the ends thereof.

Figure 4:
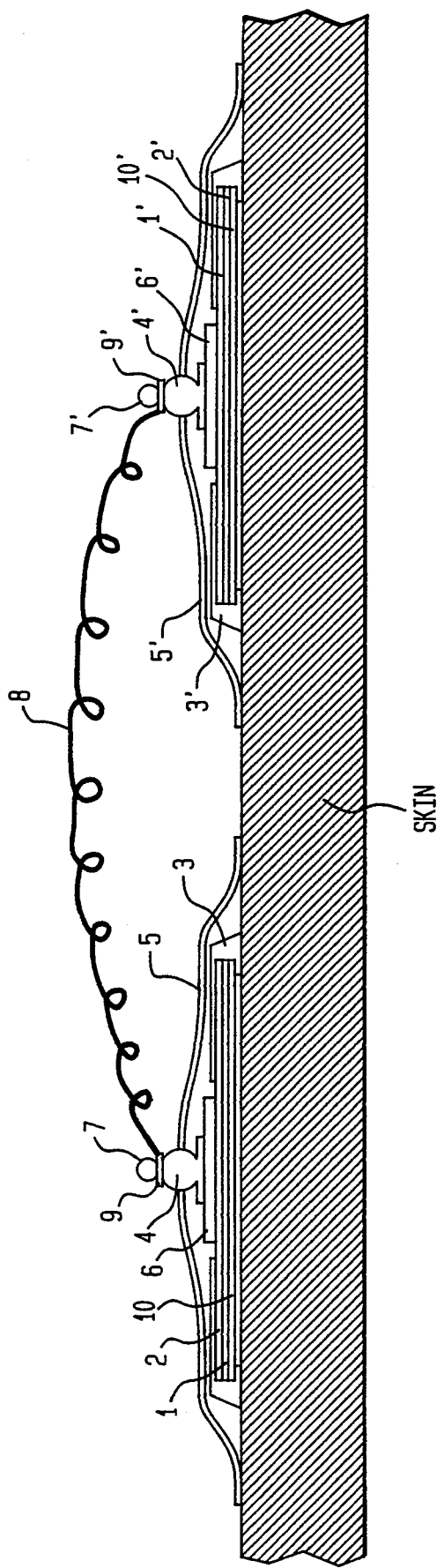
FIG. 4 is an illustration of a further example of a patch arrangement according to the invention.

For application on patients with sensitive skin, it is possible to substitute both skin contact electrodes (1, 2') with those made of same skin compatible and electrically conductive material. Since the galvanic element of both these electrodes yields the smaller voltage fraction compared to the other two galvanic elements (2, 6, 4 and 1', 6', 4'), the basic concept of the invention remains unaltered. It is also possible to incorporate carrier soaked with an electrolyte, such as moist blotting paper soaked with soda, between skin contact electrodes (1, 2') and the skin as shown in FIG. 4 by reference numerals (10, 10').

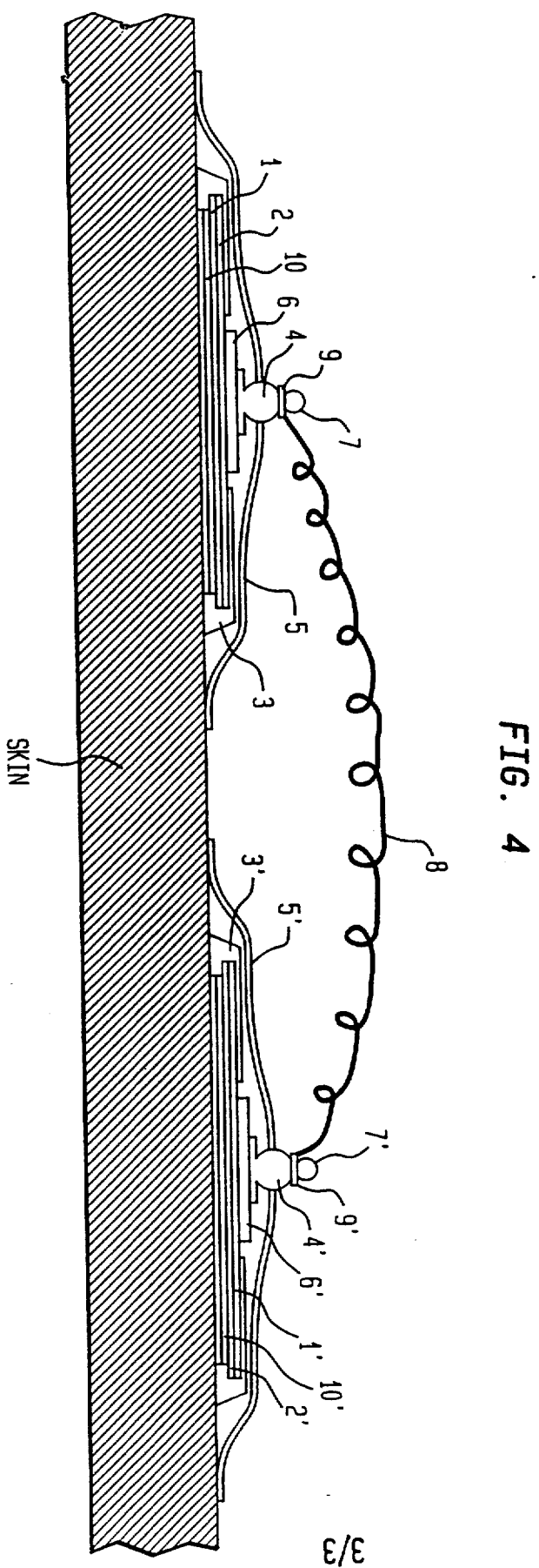

I claim:

1. A patch arrangement for application onto the skin for galvanic treatment, comprising:
    a first double-layered electrode including a skin-proximate layer of a noble metal and a skin-distant layer of a noble metal;
    a second double-layered electrode including a skin-proximate layer of a noble metal differing from the noble metal of said skin-proximate layer of said first electrode and a skin-distant layer of a noble metal differing from the noble metal of said skin-distant layer of said first electrode; and
    connection means for electrically connecting said first and second electrodes.

2. A patch arrangement as defined in claim 1, and further comprising an insulation attached to a border area of each of said first and second electrodes.

3. A patch arrangement as defined in claim 1 wherein said connection means includes a cable, and further comprising a variable electric resistor incorporated in said cable.

4. A patch arrangement as defined in claim 1 wherein said connection means includes an elastic cable.

5. A patch arrangement as defined in claim 1 wherein said noble metal for use in said first and second electrodes is a high-grade, readily skin compatible and electrically conductive metal.

6. A patch arrangement as defined in claim 1, and further comprising a carrier soaked with an electrolyte and sandwiched between said skin proximate layers of said first and second electrodes and the skin.

7. A patch arrangement as defined in claim 6 wherein said electrolyte is moist blotting paper soaked with soda.

8. A patch arrangement for application onto the skin for galvanic treatment, comprising:
    a) a first electrode patch including
        a skin-proximate layer of a noble metal,
        a skin-distant layer of a noble metal attached to said skin-proximate layer, and
        a silver electrode provided with a silver chloride gel pad applied upon said skin-distant layer;
    b) a second electrode patch including
        a skin-proximate layer of a noble metal differing from the noble metal of said skin-proximate layer of said first electrode patch,
        a skin-distant layer attached to said skin-proximate layer of said second electrode and being of a noble metal differing from the noble metal of said skin-distant layer of said first electrode patch, and
        a silver electrode provided with a silver chloride gel pad applied upon said skin-distant layer of said second electrode; and
    c) connection means for electrically connecting said first and second electrode patches.

* * * * *

UNITED STATES PATENT AND TRADEMARK OFFICE
CERTIFICATE OF CORRECTION

PATENT NO. : 5,354,321

DATED : October 11, 1994

INVENTOR(S) : Mario Bergner

It is certified that error appears in the above-identified patent and that said Letters Patent is hereby corrected as shown below:

Cover page, [76], change the name of the inventor to
-- Mario Bergner --.

The sheet of drawing, consisting of figure 4, should be deleted to be replaced with the attached sheet.

Signed and Sealed this

Ninth Day of May, 1995

Attest:

BRUCE LEHMAN

Attesting Officer

Commissioner of Patents and Trademarks